United States Patent
Leistner et al.

(10) Patent No.: US 7,304,017 B2
(45) Date of Patent: *Dec. 4, 2007

(54) SORBENT FOR USE IN PROCESS OF SOLID PHASE EXTRACTION

(75) Inventors: Aniela Leistner, Birkenstein (DE); André Leistner, Birkenstein (DE)

(73) Assignee: Polymerics GmbH, Berlin (DE)

( * ) Notice: Subject to any disclaimer, the term of this patent is extended or adjusted under 35 U.S.C. 154(b) by 46 days.

This patent is subject to a terminal disclaimer.

(21) Appl. No.: 11/117,671

(22) Filed: Apr. 28, 2005

(65) Prior Publication Data

US 2006/0138052 A1    Jun. 29, 2006

(30) Foreign Application Priority Data

Dec. 28, 2004    (DE) .................... 10 2004 063 633

(51) Int. Cl.
    *B01J 20/00* (2006.01)
(52) U.S. Cl. ..................... 502/402; 210/692
(58) Field of Classification Search ............... 210/692; 502/402

See application file for complete search history.

(56) References Cited

U.S. PATENT DOCUMENTS

| 4,202,775 A | * | 5/1980 | Abe et al. .................. 210/287 |
| 2003/0027879 A1 | * | 2/2003 | Davankov et al. ............ 521/82 |
| 2006/0058413 A1 | | 3/2006 | Leistner et al. ............. 523/105 |

FOREIGN PATENT DOCUMENTS

| DE | 100 06 590 A1 | 8/2001 |
| EP | 0 234 129 B1 | 9/1987 |
| IE | 0 059 565 B | 3/1994 |
| WO | WO 2004/060554 A1 | 7/2004 |

OTHER PUBLICATIONS

Oasis Sample Extraction Products, Waters Inc., P/N 720000606EN, (2003).
Römpp Chemie Lexikon, Thieme Verlag, Stuttgart New York, (1995).
Pielichowski J.J., Puszynski A.A., Technologia Tworzyw Sztucznych, Wydawnictwa WNT, Warszawa/Poland (1994).
John Wiley & Sons, Inc., "Sample Preparation Techniques in Analytical Chemistry", 2003, pp. 78-138, edited by: Somenath Mitra, Department of Chemistry and Environmental Science, New Jersey Institute of Technology.

* cited by examiner

*Primary Examiner*—Chester T. Barry
(74) *Attorney, Agent, or Firm*—Collard & Roe, P.C.

(57) ABSTRACT

A sorbent comprising a spherical, highly porous polymer with specific hydrophobic-hydrophilic properties, specific pore volume and its distribution, as well as a method of solid phase extraction using said sorbent. The sorbent is produced by suspension polymerization of at least one hydrophilic monomer and at least one hydrophobic monomer, where the hydrophilic monomer comprises an imidazole moiety and the hydrophobic monomer is a mixture of isomeric divinylbenzene monomers and isomeric ethylvinylbenzene monomers. The sorbent has a pore diameter range from 5 Å to 1000 Å, an average pore diameter of 50 Å to 250 Å, and a pore volume from 1 ml/g to 2 ml/g comprising 15% to 25% micropores, 50% to 80% mesopores, and 5% to 30% macropores. Solid phase extraction columns and plates packed with the sorbent of this invention provide reliable high recoveries for a broad spectrum of analytes with various polarity, even if the sorbent is dried out multiple times during the extraction.

8 Claims, 1 Drawing Sheet

Basic principle of solid phase extraction

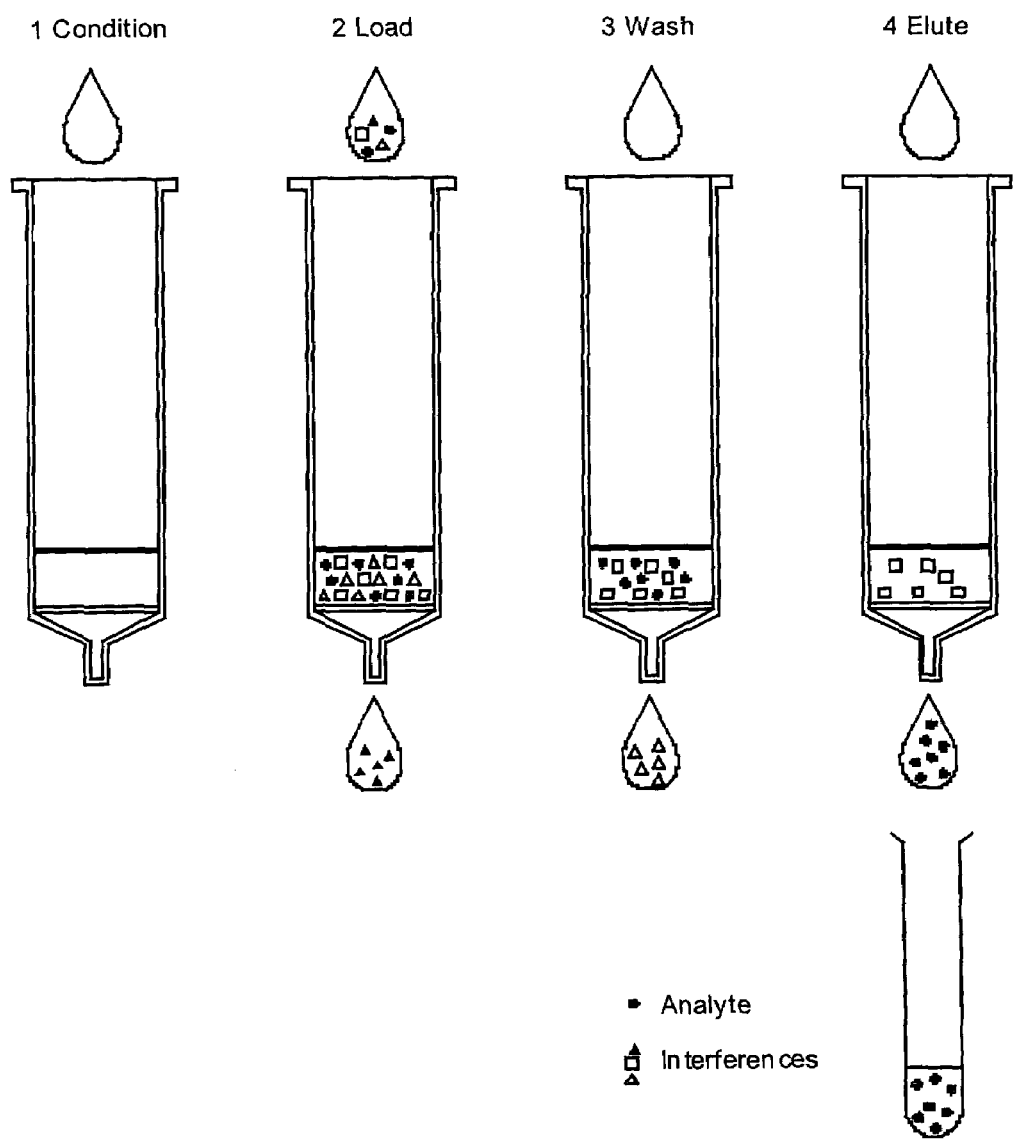
Figure 1: Basic principle of solid phase extraction

SORBENT FOR USE IN PROCESS OF SOLID PHASE EXTRACTION

CROSS REFERENCE TO RELATED APPLICATIONS

Applicants claim priority under 35 U.S.C. 119 of German Application No. 10 2004 063 633.8 filed Dec. 28, 2004.

BACKGROUND OF THE INVENTION

The present invention relates to a novel sorbent comprising a spherical, highly porous polymer, and a process of solid phase extraction comprising the use of the novel sorbent.

Solid phase extraction is a sample preparation method that has seen rapid development during the last 15 years and has been established as a standard procedure in pharmaceutical and medical research, food chemistry, and environmental analytics. Solid phase extraction owes its rise to its versatility, economic efficiency, and easy automation. It is used for sample purification, sample concentration, solvent exchange (e.g. an analyt can be transferred from aqueous solution to an organic solution), desalinization, derivatization (an analyt is retained on the sorbent, derivatized, and then eluted), and for pre-separation e.g. into various substance classes.

The development of new combinatorial methods and fast analytical techniques such as liquid chromatography/mass spectrometry (LC-MS) has led to a significant acceleration in the development of new drugs. Regular creation of thousands of samples has driven the demand for methods that allow for high throughput in automated sample preparation in order to feed analytical methods and drug screening methods with purified samples. Solid phase extraction meets this challenge by providing powerful phases in 96-well and 384-well plate formats.

In modern trace analytics, sample preparation is often more important for the quality of the result than the instrumental analytical method used. This is especially true when analyzing traces in samples with complex compositions such as body fluids, biological tissues, food, extracts of natural products, and others. For such applications, solid phase extraction provides a time saving, reproducible alternative to otherwise used liquid-liquid extraction.

Solid phase extraction is an easily applied method using simple extraction cartridges of various dimensions, or high-throughput extraction plates in 96- or 384-well plate formats [Oasis Sample Extraction Products, Waters Inc., P/N 720000606EN, (2003)]. The basic principle of solid phase extraction is shown in FIG. 1. In a first step, the sorbent is typically conditioned. Then the usually aqueous sample solution is added to the top of the extraction cartridge (loading). While the sample solution flows through the sorbent bed, solutes are retained by the sorbent and thus extracted. Interferences (accompanying matrix substances) can then be removed selectively by choosing a suitable wash solution. Finally, the solute of interest is eluted selectively using a suitable solvent.

Alternatively to the process described above, the extraction cartridge can also be used to selectively retain sample impurities while the solute passes the sorbent unretained [Mitra, S. (editor), Sample preparation techniques in analytical chemistry, John Wiley & Sons (2003), p. 78-138].

In many applications solid phase extraction is used to concentrate the solute. To do so, a large volume of aqueous sample solution with low solute concentration is filtered through the sorbent and subsequently eluted with a small volume of organic solvent (usually methanol). In the ideal case, the complete amount of solute from the original aqueous solution will be contained in the methanol eluate.

Solid phase extraction cartridges are typically packed with sorbents having average particle sizes of 30 μm and 60 μm. Many solutions flow through the cartridge under the force of gravity. In order to treat solutions with higher viscosity one of the following methods is used:
vacuum at the outlet (lower end) of the cartridge
centrifugation of the sample through the cartridge
positive pressure at the inlet (upper end) of the cartridge
These methods are also recommended if the sorbent particle size is below 50 μm.

Most frequently a vacuum manifold is used to perform solid phase extraction. Positive pressure is only used when treating singular solutions, or in fully automated solid phase extraction systems. Manual addition of the sample using an injection syringe requires a cartridge adapter.

The most commonly used sorbents for solid phase extraction are based on so-called silica gel reverse phases (RP phases) whose polar surface has been modified with aliphatic, cycloaliphatic, and aromatic carbohydrates described in IE 0 059 565 B, EP 0 234 129 B1, and U.S. Pat. No. 4,680,121. These sorbents exhibit a number of disadvantages. They are unstable above pH=10 and below pH=2. They have to remain wetted during the full extraction procedure. Upon contact with purely aqueous solutions they exhibit a strong tendency to collapse. Such sorbents which have dried out or collapsed display poor retentions of analytes and therefore poor recovery.

The requirement that the sorbent remain wetted during the extraction process complicates the solid phase extraction process and significantly extends analysis time since instruments for automated solid phase extraction have to be equipped with additional sensors and safeguards to prevent drying out of the sorbent.

Copolymers of styrene and divinylbenzene are also known as polymer-based sorbents for solid phase extraction in addition to silica gel materials (U.S. Pat. No. 4,167,554, U.S. Pat. No. 4,495,250, U.S. Pat. No. 5,773,384). These polymer sorbents have strongly hydrophobic surface properties and display excellent pH resistance. However, similar to silica gel reversed phases, they must not dry out during the extraction process. If this requirement is not met, styrene-divinylbenzene-copolymers display poor recoveries for a number of substance classes.

Further progress in the field of polymer sorbents for solid phase extraction has been attained by U.S. Pat. No. 5,882,521 describing water-wettable polymer sorbents which have been introduced to the market in 1997. These sorbents are macroporous copolymers comprising two monomer components, the lipophilic divinylbenzene, and the hydrophilic N-vinylpyrrolidone, where the two monomers are present in a hydrophilic-hydrophobic balance (HLB). Because of its water-wettability this copolymer retains its capacity for strong retention of a broad spectrum of various analytes with good recoveries, even if the material dries out. In the dried out state, this copolymer shows much better retention (recovery greater than 85%) for polar analytes such as acetaminophen, ranitidine, or procainamide, than hydrophobic styrene-divinylbenzene-copolymers, and significantly better than classic silica gel C18 phases.

However, problems can arise with N-vinylpyrrolidone-divinylbenzene-copolymers when using strongly basic liquids as solvent, wash solution, or eluent. It is known that poly(N-vinylpyrrolidone) undergoes hydrolysis in the presence of bases to form poly(N-vinyl-aminobutyric acid) according to the following equation:

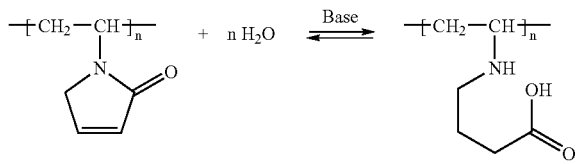

[Pielichowski J. J., Puszynski A. A., Technologia Tworzyw Sztucznych, Wydawnictwo WNT, Warszawa/Poland (1994)].

This reaction threatens the stability of the sorbent in basic environments. Moreover, the synthesis of N-vinylpyrrolidone-divinylbenzene-copolymers causes another problem since N-vinylpyrrolidone has been shown to be carcinogenic in animal tests [Römpp Chemie Lexikon, Thieme Verlag, Stuttgart N.Y., (1995)].

Thus, there is need for an alternative hydrophobic-hydrophilic polymer sorbent material which can be synthesized in an environmentally friendly way, exhibits high stability in basic and acidic media, and can be used as a universal solid phase extraction material in modern processes of solid phase extraction including high-throughput methods.

DETAILED DESCRIPTION OF THE INVENTION

The present invention provides a highly porous polymer sorbent, consisting of spherical particles, obtained from suspension polymerization of at least one hydrophilic monomer and at least one hydrophobic monomer where
- the hydrophilic monomer contains an imidazole moiety
- the hydrophobic monomer is a mixture of divinylbenzene and ethylvinylbenzene
- the polymer has a pore diameter range from 5 Å to 1000 Å with an average pore diameter from 50 Å to 250 Å and a pore volume from 1 ml/g to 2 ml/g
- the pore size distribution (based on pore volume) is composed of 15% to 25% micropores, 50% to 80% mesopores, and 5% to 30% macropores.

The present invention further includes a process of solid phase extraction by using the sorbent of the present invention.

Suitable hydrophilic monomers are, for example, 1-vinylimidazole, 4-vinylimidazole, 1-vinyl-2-methylimidazole, 1-vinyl-2-ethylimidazole, 1-propenyl-2-methylimidazole, and 1-allyl-2-methylimidazole, which are incorporated into the polymer network by radical co- and terpolymerization.

Suitable hydrophobic monomers are mixtures of isomeric divinylbenzene and isomeric ethylvinylbenzene, comprising from 50 wt % to 85 wt % divinylbenzene and from 5 wt % to 40 wt % ethylvinylbenzene, which are incorporated into the polymer network by radical co- and terpolymerization.

A preferred embodiment of this invention comprises further functional monomers such as acrylic acid, methacrylic acid and/or their alkyl esters and/or their alkyl amides, which are incorporated into the polymer network from 0 wt % to 20 wt % by radical co- and terpolymerization. Suitable functional monomers comprise methyl acrylate, ethyl acrylate, butyl acrylate, 2-hydroxyethylmethacrylate, 2-hydroxypropylmethacrylate, N,N-dimethylaminopropylmethacrylate, N,N-dimethylaminoethylmethacrylate, 3-sulfopropylacrylate potassium salt, acrylamide, methacrylamide, isopropylamide, triethyleneglycoldimethacrylate, and diethyleneglycoldimethacrylate.

A particularly preferred embodiment of this invention comprises co- and terpolymers having 6 wt % to 12 wt % of various vinylimidazoles incorporated into the material by radical co- and terpolymerization.

It is a particular advantage that the spherical sorbents of this invention are tailored, highly porous, hydrophobic-hydrophilic spherical particles with an average pore diameter from 50 Å to 250 Å and a specific pore size distribution. It has been surprisingly found that the sorbents of this invention should not only have a certain monomer composition but also a certain pore size distribution in order to fulfil their tasks quickly and reliably in modern methods of solid phase extraction. Adsorption speed and adsorption capacity are properties which are governed by pore size distribution.

According to IUPAC (International Union of Pure and Applied Chemistry) micropores are defined as pores with pore diameters below 20 Å, mesopores are pores between 20 Å and 500 Å, and macropores are pores with diameters greater than 500 Å. Pore size distribution, total pore volume and specific surface can be determined using measurements of nitrogen adsorption at the boiling temperature of nitrogen (77 K), which have been conducted for the sorbents of this invention using an ASAP 2010 device (Micromeritics Instrument Corporation, Norcross, Ga., USA). For micro- and macroporous sorbents these measurements deliver characteristic adsorption and desorption isotherms, characterized by a hysteresis.

Specific surface is calculated from the adsorption and desorption isotherms using the BET multilayer adsorption isotherm. Determination of mesopores and macropores up to 1500 Å is conducted using a procedure developed by Barrett, Joyner, and Halenda—the so-called BJH method. Determination of micropore volume and its distribution is conducted using the adsorption isotherm based on the method of Horvath-Kawazoe. The total pore volume is determined from the nitrogen volume adsorbed by the sorbent at a relative pressure $p/p0=0.99$ and transformation to the volume of liquid nitrogen.

It is a particular advantage of the polymer sorbents of this invention that they have a total pore volume ranging from 1 ml/g to 2 ml/g comprising from 15 vol % to 25 vol % micropores, 50 vol % to 80 vol % mesopores, and 5 vol % to 25 vol % macropores.

Sorbents which only comprise mesopores and macropores show slow adsorption, low capacity, and therefore, they are not suitable for high-throughput methods of solid phase extraction. Sorbents which only comprise micropores also show slow adsorption. Additionally, they poorly remove analytes from complex matrices such as plasma, urine, or biological tissue, and are therefore unsuitable for most applications of solid phase extraction. In contrast, the polymer sorbents of the present invention with a balanced pore size distribution between micro-, meso-, and macropores display excellent adsorption speed and high adsorption capacity for many different analytes from aqueous solutions as well as from complex matrices such as blood plasma, urine, plant extracts, or food emulsions.

The polymer sorbents of the present invention are synthesized by a specific suspension polymerization as described in DE 100 06 590.

The polymer sorbents used for the solid phase extraction of the present invention have a spherical shape with diameters in the range from 5 μm to 150 μm. Preferred embodiments of this invention comprise the use of particle diameters from 15 µm to 45 µm, and from 56 µm to 100 µm, respectively.

The polymer sorbents of this invention have a specific surface from 200 m$^2$/g to 900 m$^2$/g.

By decreasing the pH value the polymer sorbents of this invention can be equipped with suitable anion exchange properties. This results in a further advantage in that acidic analytes can be easily and selectively separated from neutral and basic analytes.

The present invention further relates to a process of solid phase extraction comprising the use of the polymer sorbents of the present invention.

Composition, particle size, and quantity of the polymer sorbent are chosen according to the volume, the analytes to be separated and the working scale of the samples. In the field of analytical solid phase extraction cartridge volumes from 1 ml to 30 ml are preferred. The polymer sorbent of this invention is packed into cartridges of 1 ml, 3 ml, 6 ml, 15 ml, or 30 ml made from polyethylene, polypropylene, polyetheretherketone, or glass, comprising a suitable micorporous filter element with preferred pore sizes from 10 µm to 45 µm, at both ends of the polymer sorbent bed. In the field of preparative solid phase extraction column volumes up to 100 l are possible. In the field of preparative solid phase extraction the polymer sorbents of this invention can also be used in a batch-stirred reactor.

The method of the present invention is particularly useful for automated application. For this, the polymer sorbent of this invention is prefereably packed in 96-well or 384-well plates.

One embodiment of the solid phase extraction of the present invention comprises the following steps:
1. Condition
2. Equilibrate
3. Load
4. Wash
5. Elute
6. Identify
7. Isolate The condition step is typically performed using water-miscible organic solvents such as methanol, ethanol, acetone, or tetrahydrofurane. They can be used in pure form or as mixtures with water. Upon eqilibration the solid phase extraction material is washed with distilled water or a buffer solution with suitable pH. Loading is performed by adding a specific volume of aqueous solution of analytes (the load solution) and subsequent filtration at a specific flow rate. When using 1 ml of load solution and cartridges packed with 60 mg of polymer sorbent the flow rate is 1 ml/min. The pH of the load solution can be adjusted using a common buffer.

The load solution can also comprise a mixture of water or an aqueous buffer and a water-miscible organic solvent, such as methanol, ethanol, acetonitrile, N,N-dimethylformamide or dimethylsulfoxide. In these cases the load solution should contain more than 50 vol % of water.

The load solution contains at least one organic solute frequently referred to as the analyte. The load solution can also comprise more than one solutes (analytes). These organic solutes can comprise medical drugs, pesticides, herbicides, herbal drugs, metabolic substances, drugs, poison, toxins, and many other polar and non-polar organic compounds. The organic compounds can also comprise biomolecules such as proteins, peptides, hormones, polynucleotides, vitamins, lipids, carbohydrates, and enzymes. These analytes can be solved in so-called complex matrices such as blood plasma, urine, other biological body fluids or tissue extracts, fruit, vegetable, and meat extracts, and food ingredients itself. Furthermore, the load solution can comprise ground water, surface water, tap water, or an aqueous or organic extract of a soil sample.

In the wash step the analytes adsorbed on the polymer sorbent are freed from contamination. Depending on the substance class and specific purpose various wash solutions can be used, for example, 5% methanol in water for neutral analytes, 5% methanol in water with pH=3 for acidic analytes, or 5% methanol in water with pH=10 for basic analytes. When washing acidic or basic analytes the wash solution can also comprise higher methanol content.

In the elution step neutral and basic analytes are usually completely desorbed from the polymer sorbent using methanol or ethanol. In the case of acidic analytes it is advisable to add an inorganic base to the methanol, for example 2% NH3 solution.

Identification and determination of recovery is typically performed using high performance liquid chromatography (HPLC), combined high performance liquid chromatography and mass spectrometry (HPLC-MS), gas chromatography (GC), combined gas chromatography and mass spectrometry (GC-MS), or in the case of singular analytes using UV-VIS spectrometry, refractometry, and other relevant methods. If desired, the eluted analytes can be isolated by gentle evacuation. Eluates containing volatile analytes, such as some amines, should be concentrated using a rotary evaporator or be acidified prior to evacuation.

In a further embodiment the solid phase extraction method of the present invention the steps of conditioning and equilibration can be omitted and the dry polymer sorbent can be brought in contact with the load solution directly. In this case a lower capacity of the polymer sorbent should be expected.

The invention will now be further described by the following examples

EXAMPLES

Example 1

1. Preparation of the Solid Phase Extraction Columns 60 mg ±2 mg of an N-vinylimidazole-divinylbenzene-copolymer comprising 6 wt % N-vinylimidazole, having a spherical particle shape, having a specific surface of 647 m$^2$/g, having an average pore diameter of 90 Å, having a total pore volume of 1.68 ml/g, having the following pore size distribution: 0.27 ml/g micropores, 1.12 ml/g mesopores, and 0.29 ml/g macropores, having a particle size distribution from 45 µm to 71 µm, were packed in 3 ml polypropylene cartridges equipped with ah HDPE filter plate (pore size 20 µm) at the lower end. Following packing, the polymer sorbent bed was enclosed with another HDPE filter plate on the top. The so-prepared cartridges are ready for use on a vacuum manifold for solid phase extraction.

2. Preparation of the Test Solution

Each model compound was dissolved in a mixture of 50 vol % methanol and 50 vol % 20 mM phosphate buffer, pH=7, to form a solution having a concentration of 10 µg/ml. The following solutions were prepared: acetaminophen, procainamide, ranitidine, caffeine, toluamide, toluidine, 2,7-dihydronaphthalene, propranolol, dipropylphthalate, and dopexin.

3. Creation of Calibration Curves
HPLC device: Waters alliance 2690 detector: UV-VIS photodiode array detector
column: Waters symmetry C18
mobile phase: methanol : buffer pH7=80:20 (v/v)
temperature: 25° C.
flow: 0.5 ml/min, isocratic By injection of 2, 4, 6, 8, and 10 μl of each analyte solution onto the HPLC column followed by electronic evaluation of the elution chromatograms linear calibration curves were created for each analyte in the expected concentration range at each analytes characteristic wavelength (maximum at longest wavelength).

4. Performing Solid Phase Extraction

Solid phase extraction was performed according to 2 protocols.

4.1 SPE Protocol 1 (Dry Method)

This protocol simulates a high-throughput environment. The sorbent is repeatedly dried out by applying vacuum. The buffer used is a 20 mmol phosphate buffer, pH=7.
1. Condition: 1 ml methanol
2. Equilibrate: 1 ml water
3. Dry: 2 min full vacuum
4. Load: 1 ml test solution (10 μg analyte in 1 ml buffer)
5. Wash: 1 ml buffer
6. Dry: 2 min full vacuum
7. Elute: 1 ml methanol, collect eluate in 2 ml volumetric flask
8. Preparation for analysis: fill up the volumetric flask with buffer 4.2 SPE Protocol 2 (Wet Method)

This protocol simulates the conditions used for silica gel RP phases as a solid phase extraction material. Drying out of the sorbent must be prevented completely in this case. In each step, the solutions or solvents used are only allowed to flow through the sorbent until they reach the upper edge of the sorbent bed so that the sorbent remains wetted. The buffer used is a 20 mmol phosphate buffer, pH=7.
1. Condition: 1 ml methanol
2. Equilibrate: 1 ml water
3. Load: 1 ml test solution (10 μg analyte in 1 ml buffer)
4. Wash: 1 ml buffer
5. Elute: 1 ml methanol, collect eluate in 2 ml volumetric flask
6. Preparation for analysis: fill up the volumetric flask with buffer 4.3 Determination of Recovery Using HPLC and the corresponding calibration curves the amount of eluted analyte was determined and compared with the amount in the test solution. This ratio, multiplied by 100%, gives the percent recovery for the investigated analyte. Determination of recovery of each analyte was performed 3 times and an average value was calculated. The obtained recoveries of the polymer sorbent of this invention (NVI-DVB-CP) are compared with a reference material (NVP-DVB-CP) in table 1.

TABLE 1

Comparison of SPE percent recoveries for various model compounds
Analyses performed 3 times. NVI = N-vinylimidazole,
NVP = N-vinylpyrrolidone, DVB = divinylbenzene,
CP = copolymer

| Compound | Percent recovery (dry method) | | Percent recovery (wet method) | |
| --- | --- | --- | --- | --- |
| | NVI-DVB-CP | NVP-DVB-CP | NVI-DVB-CP | NVP-DVB-CP |
| Acetaminophen | 91.6 | 98.0 | 99.3 | 99.3 |
| Procainamide | 97.1 | 100.0 | 98.0 | 100.7 |
| Caffeine | 91.0 | 89.0 | 97.9 | 93.5 |
| Ranitidine | 96.0 | 93.1 | 97.1 | 92.9 |
| Toluamide | 97.7 | 90.7 | 98.0 | 92.2 |
| Toluidine | 96.0 | 93.0 | 95.0 | 92.5 |
| 2,7-Dihydroxy-naphthaline | 106.7 | 105.6 | 97.3 | 95.6 |
| Propranolol | 101.0 | 99.7 | 100.5 | 97.2 |
| Dipropyl-phthalate | 95.0 | 93.0 | 94.5 | 92.0 |
| Doxepin | 90.0 | 88.0 | 90.0 | 94.4 |

Table 1 shows that the NVI-DVB-copolymer sorbent of this invention delivers comparable or slightly better high recoveries vor various polar analytes compared with the reference material, an NVP-DVB-copolymer, both under drastic (dry) as well as optimum (wet) conditions.

Since N-vinylimidazole does not exhibit carcinogenic effects, the synthesis of N-vinylimidazole-divinylbenzene is more human friendly and environmentally friendly. As such the NVI-DVB-copolymers of this invention provide an environmentally friendly alternative to NVP-DVB-copolymers.

Example 2

Comparison of Recoveries with Another SPE Sorbent

The polymer sorbent of this invention as used in example 1 has been tested in comparison with a C18-RP silica gel material and a hydrophobic styrene-divinylbenzene copolymer. In contrast to example 1, the solid phase extraction cartridges used had a volume of 6 ml, and they were packed with 200 mg sorbent material between HDPE filter plates (pore size 20 μm). Solid phase extraction was performed according to protocol 1, i.e. including drying out the sorbent bed twice. Because of the greater volume of sorbents used, the volumes of test solutions and solvents of each step were increased to 4 ml. Determination of recovery was conducted analogous to example 1 and is presented in table 2.

TABLE 2

Comparison of percent recoveries for various model compounds (dry method). Analyses performed 3 times. NVI = N-vinylimidazole, DVB = divinylbenzene, CP = copolymer

| Compound | Percent recovery | | |
|---|---|---|---|
| | NVI-DVB-CP | C18-RP Phase | Styrene-DVB-CP |
| Acetaminophen | 90 | 71 | 13 |
| Caffeine | 96 | 97 | 98 |
| Procainamide | 105 | 0 | 37 |
| Propranolol | 101 | 0 | 101 |
| Resorcinol | 85 | 15 | 22 |
| Phenol | 106 | 85 | 105 |
| p-Toluidine | 95 | 89 | 90 |

Table 2 shows that the NVI-DVB-copolymer sorbents of this invention show reliable high recoveries (greater 85%) of a broad spectrum of analytes even after drying out the sorbent twice. In the case of the silica gel C18-RP phase and hydrophobic styrene-DVB-copolymer this reliability and safety is not achieved.

Upon using the the polymer sorbent of this invention it was surprisingly found that drying out the sorbent—no matter during which step of solid phase extraction—does not lead to problems so that the method could be evaluated as very reliable.

What is claimed is:

1. A sorbent comprising a spherical, highly porous polymer, said polymer being formed by suspension polymerization of at least one hydrophilic monomer and at least one hydrophobic monomer, wherein:
   the hydrophilic monomer contains an imidazole moiety,
   the hydrophobic monomer is a mixture of isomeric divinylbenzene and isomeric ethylvinylbenzene monomers,
   the sorbent has a pore diameter range from 5 Å to 1000 Å and an average pore diameter from 50 Å to 250 Å,
   the sorbent has a pore volume from 1 ml/g to 2 ml/g, and
   the pore volume comprises 15% to 25% micropores, 50% to 80% mesopores, and 5% to 30% macropores.

2. The sorbent of claim 1, comprising 5 wt % to 25 wt % of the monomer containing the imidazole moiety.

3. The sorbent of claim 1, comprising 60 wt % to 95 wt % of the mixture of divinylbenzene and ethylvinylbenzene.

4. A sorbent of claim 1, formed by radical copolymerization or terpolymerization of 1-vinylimidazole, 4-vinylimidazole, 1-vinyl-2-methylimidazole, 1-vinyl-2-ethylimidazole, 1-propenyl-2-methylimidazole, or 1-allyl-2-methylimidazole, with a mixture of divinylbenzene and ethylvinylbenzene, and optionally comprising a further functional monomer, preferably acrylic acid or methacrylic acid and/or their alkyl esters or alkyl amides.

5. The sorbent of claim 1, wherein the divinylbenzene monomer is a mixture of isomers and said sorbent comprises 50 wt % to 85 wt % of the divinylbenzene monomer.

6. The sorbent of claim 1, wherein the ethylvinylbenzene monomer is a mixture of isomers and said sorbent comprises 5 wt % to 40 wt % of the ethylvinylbenzene monomer.

7. The sorbent as claimed in claim 1, comprising a copolymer of N-vinylimidazole and divinylbenzene, said copolymer comprising 5 wt % to 25 wt % of N-vinylimidazole.

8. The sorbent as claimed in claim 1, wherein said sorbent has an average particle size from 5 μm to 150 μm and a specific surface from 200 $m^2$/g to 900 $m^2$/g.

* * * * *